United States Patent [19]

Kreuder et al.

[11] Patent Number: 5,621,131

[45] Date of Patent: Apr. 15, 1997

[54] CONJUGATED POLYMERS HAVING SPIRO CENTERS AND THEIR USE AS ELECTROLUMINESCENCE MATERIALS

[75] Inventors: Willi Kreuder, Mainz; Donald Lupo, Frankfurt; Josef Salbeck, Kelkheim; Hermann Schenk, Hofheim; Thomas Stehlin, Kriftel, all of Germany

[73] Assignee: Hoechst Aktiengesellschaft, Frankfurt, Germany

[21] Appl. No.: 541,237

[22] Filed: Oct. 12, 1995

[30] Foreign Application Priority Data

Oct. 14, 1994 [DE] Germany .................. 44 36 773.2

[51] Int. Cl.⁶ .......................... C07C 22/00; C08G 59/00
[52] U.S. Cl. ..................... 558/46; 528/403; 528/405; 528/406; 528/408; 528/420; 528/423; 528/425
[58] Field of Search ............................. 558/46; 528/403, 528/405, 406, 408, 420, 423, 425

Primary Examiner—Samuel A. Acquah
Attorney, Agent, or Firm—Curtis, Morris & Safford

[57] ABSTRACT

Conjugated polymers comprising recurring units of the formula (I),

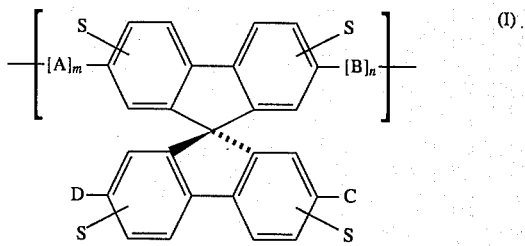

A, B, C, D are identical or different and are each from one to fifteen identical or different arylene and/or heteroarylene and/or vinylene groups which, like the spirobifluorene skeleton itself, may be unsubstituted or substituted;

S are identical or different substituents;

m, n are 0 or 1.

The polymers of the invention having the formula (I) are suitable as electroluminescence materials and have, in particular, a high color purity of the emission.

8 Claims, 2 Drawing Sheets

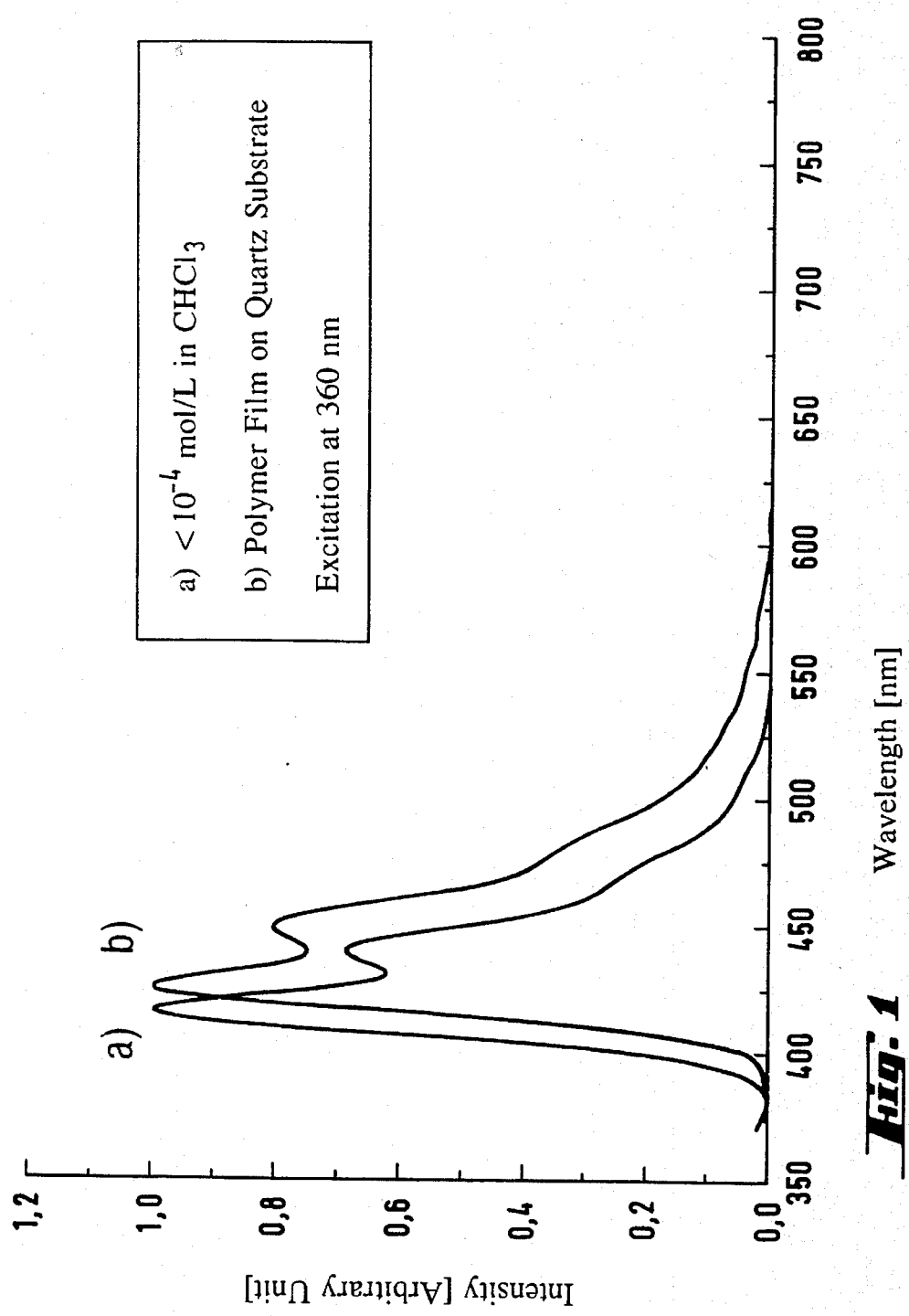

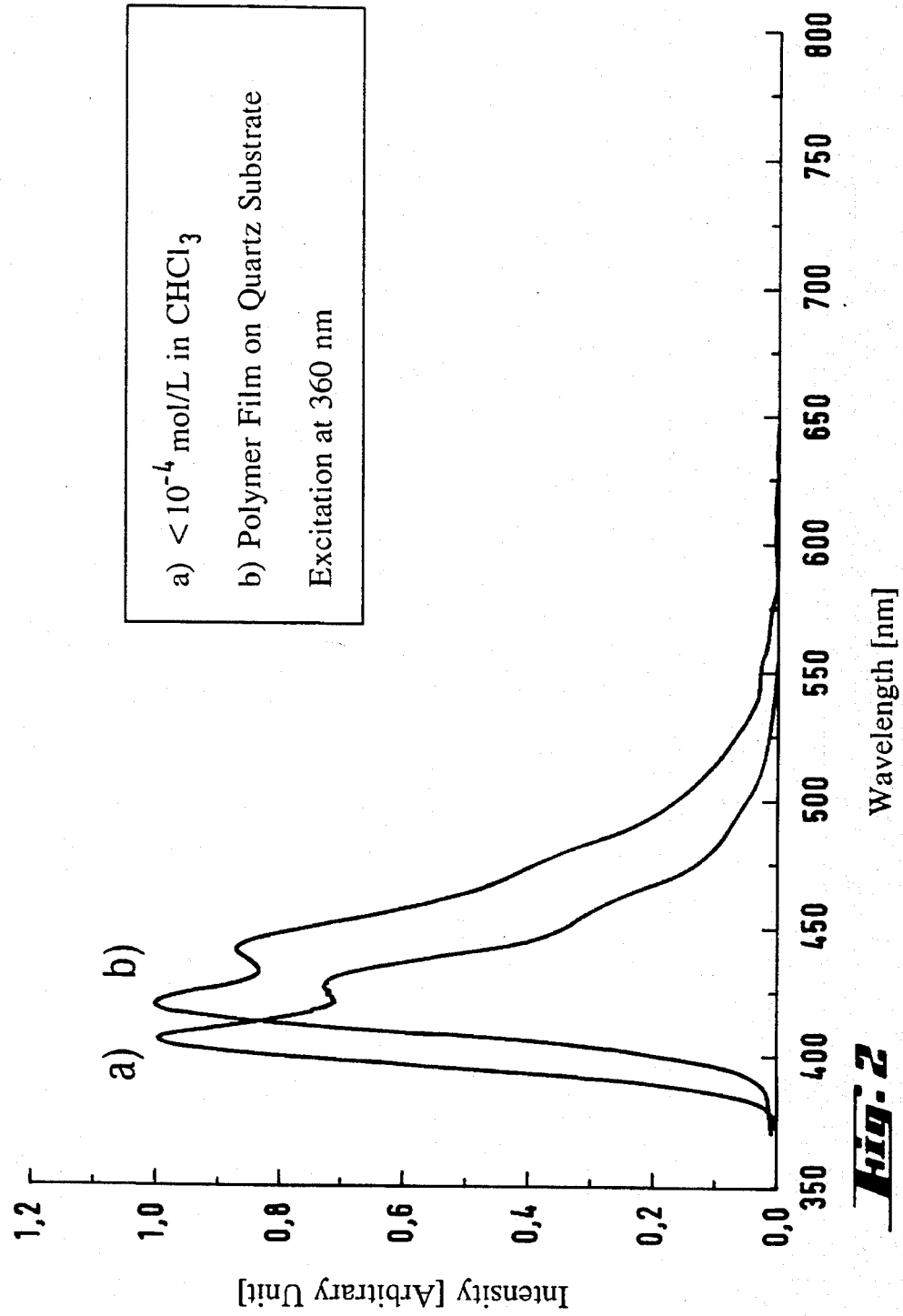

CONJUGATED POLYMERS HAVING SPIRO CENTERS AND THEIR USE AS ELECTROLUMINESCENCE MATERIALS

There is a great industrial need for large-area solid state light sources for a series of applications, predominantly in the field of display elements, VDU technology and lighting engineering. The demands made of these light sources can at present not be completely satisfactorily achieved by any of the existing technologies.

As an alternative to conventional display and lighting elements, such as incandescent lamps, gas-discharge lamps and non-self-illuminating liquid crystal display elements, use has been made for some time of electroluminescence (EL) materials and devices, such as light-emitting diodes (LEDs).

Apart from inorganic materials, low molecular weight organic electroluminescence materials and devices have been known for about 30 years (see, for example, U.S. Pat. No. 3,172,862). Until recently, however, such devices had a very limited practical usability.

WO 90/13148 and EP-A 0 443 861 describe electroluminescence devices containing a film of a conjugated polymer as light-emitting layer (semiconductor layer). Such devices offer numerous advantages such as the opportunity of producing large-area, flexible displays simply and inexpensively. In contrast to liquid crystal displays, electroluminescence displays are self-illuminating and therefore require no additional backward lighting source.

A typical device according to WO 90/13148 comprises a light-emitting layer in the form of a thin, dense polymer film (semiconductor layer) which contains at least one conjugated polymer. A first contact layer is in contact with a first surface, a second contact layer with a further surface of the semiconductor layer. The polymer film of the semiconductor layer has a sufficiently low concentration of extrinsic charge carriers so that, on application of an electric field between the two contact layers, charge carriers are introduced into the semiconductor layer, which makes the one contact layer positively charged compared with the other and the semiconductor layer emits radiation. The polymers used in such devices are conjugated. For the purposes of the present invention, a conjugated polymer is a polymer possessing a delocalized electron system along the main chain. The delocalized electron system gives the polymer semiconducting properties and enables it to transport positive and/or negative charge carriers with high mobility.

In WO 90/13148, the polymeric material used for the light-emitting layer is poly(p-phenylenevinylene), and it is proposed that the phenyl group in such a material be replaced by a heterocyclic or a condensed carbocyclic ring system. In addition, poly(p-phenylene), PPP, is also used as electroluminescing material (G. Grem, G. Leditzky, B. Ullrich, G. Leising, Synth. Met. 1992, 51, page 383).

Although good results have been obtained with these materials, the color purity, for example, is still unsatisfactory. Furthermore, with the polymers known hitherto it is hardly possible to generate a blue or white emission.

Since, in addition, the development of electroluminescence materials, particularly on the basis of polymers, can in no way be regarded as being concluded, the manufacturers of lighting and display devices are interested in a great variety of electroluminescence materials for such devices.

This is, inter alia, because only the combined action of the electroluminescence materials with the further components of the devices allows conclusions to be drawn on the quality of the electroluminescence material.

It is therefore an object of the present invention to provide new electroluminescence materials which are suitable, when used in lighting or display devices, of improving the property profile of these devices.

It has now surprisingly been found that conjugated polymers whose recurring units contain a 9,9'-spirobifluorene skeleton have not only an improved solubility in organic solvents and improved film-forming properties but also, in particular, have good electroluminescence and photoluminescence with a high color purity.

Spirocompounds are compounds in which two ring systems are linked by a single tetravalent atom. This atom is referred to as a spiro atom, as explained in Handbook of Chemistry and Physics, 62nd edition (1981-2), CRC Press, pages C-23 to C-25.

Compounds in which two polymers are linked via a single spiro atom are proposed, for example in U.S. Pat. No. 5,026,894 and in J. M. Tour et al., J. Am. Chem. Soc. 1990, 112, 5662; J. M. Tour et al., J. Am. Chem. Soc. 1991, 113, 7064; J. M. Tour et al., Polym. Prepr. 1990, 408 as materials for molecular electronics. Possible suitability of such compounds as electroluminescence materials cannot be derived therefrom.

The invention accordingly provides conjugated polymers comprising recurring units of the formula (I),

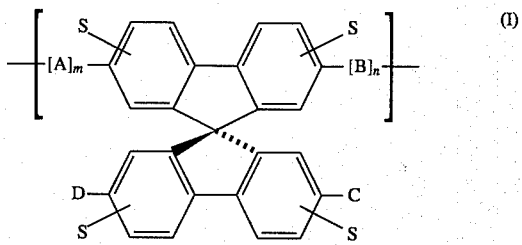

(I)

A, B, C, D are identical or different and are each from one to fifteen identical or different arylene and/or heteroarylene and/or vinylene groups which, like the spirobifluorene skeleton itself, may be unsubstituted or substituted;

S are identical or different and are each H or a substituent; are 0 or 1.

The polymers of the invention have, in particular, a high color purity of the emission.

For the purposes of the invention, a polymer is a compound whose electroluminescence spectrum is essentially unchanged on attaching further recurring units.

The polymers of the invention generally have from 2 to 1000, preferably from 2 to 500, particularly preferably from 2 to 100, recurring units of the formula (I).

Furthermore, preference is given to those polymers in which the symbols and indices in the formula (I) have the following meanings:

S are identical or different and are $R^1$, $R^2$, $R^3$ and/or $R^4$;

A, B are identical or different and are

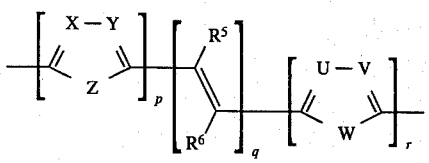

-continued

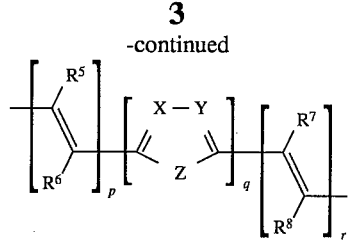

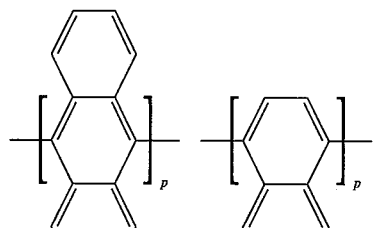

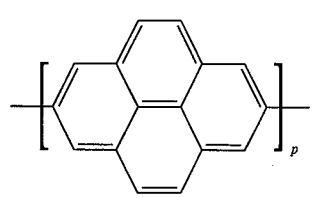

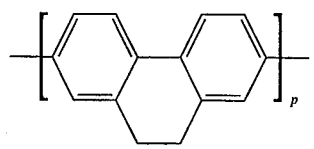

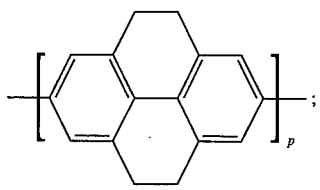

X, Y, U, V are identical or different and are $CR^5$, N;

Z, W are identical or different and are —O—, —S—, —$NR^5$—, —$CR^5R^6$—, —$CR^5=CR^6$—, —$CR^5=N$—;

p, q, r are identical or different and are 0, 1 to 5;

$R^1$, $R^2$, $R^3$, $R^4$, $R^5$ $R^6$, $R^7$, $R^8$ are identical or different and are each H, a straight-chain or branched alkyl, alkoxy or ester group having from 1 to 22 carbon atoms, aryl and/or aryloxy groups, preferably phenyl and/or phenyloxy groups, where the aromatic can be substituted by $C_1$–$C_{22}$-alkyl, $C_1$–$C_{22}$-alkoxy, Br, Cl, F, CN, and/or $NO_2$, Br, Cl, F, CN, $NO_2$, $CF_3$;

C, D are identical or different and are

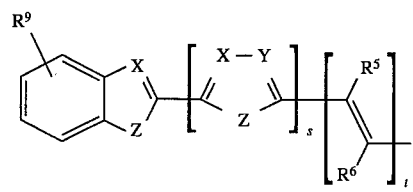

-continued

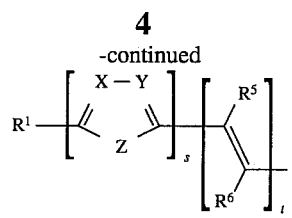

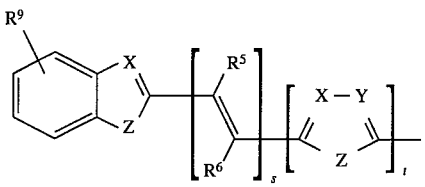

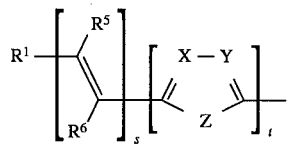

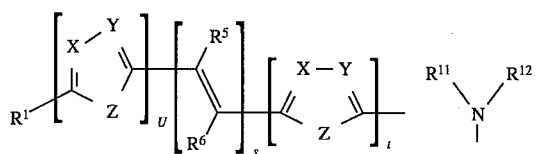

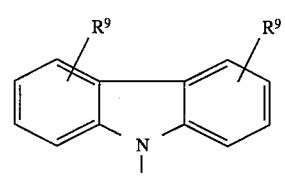

$R^9$ are identical or different and are each H, an unbranched or branched alkyl or alkoxy group having from 1 to 22 carbon atoms, —CN, —$NO_2$, —$NR^{11}R^{12}$, phenyl, biphenyl, 1-naphthyl, 2-naphthyl, 2-thienyl, 2-furanyl, where aryls and heteroaryls can bear a further substituent $R^9$;

X,Y are identical or different and are =$CR^5$—, =N—;

Z are identical or different and are —O—, —S—, —$NR^{11}$—, $CR^5R^6$, —$CR^5=CR^6$—, —$CR^5=N$—;

$R^{11}$, $R^{12}$ are identical or different and are each H, an unbranched or branched alkyl group having from I to 22 carbon atoms, phenyl, 3-methylphenyl, biphenyl, 1-naphthyl, 2-naphthyl.

Particular preference is given to polymers, in which the symbols and indices in the formula (I) have the following meanings:

A, B are identical or different and are

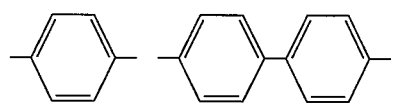

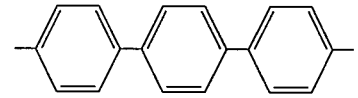

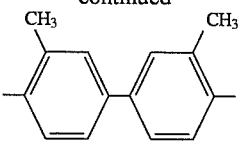
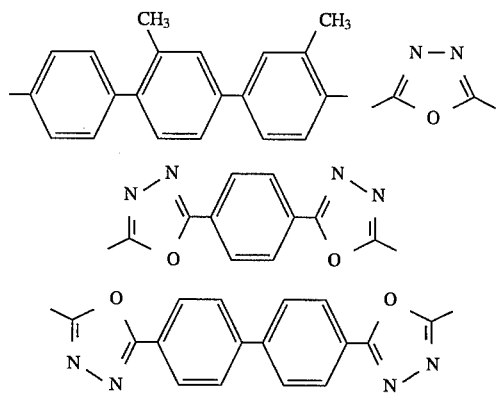
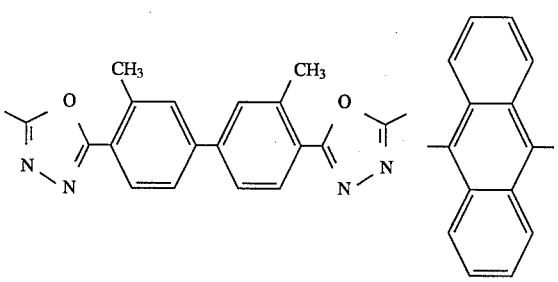
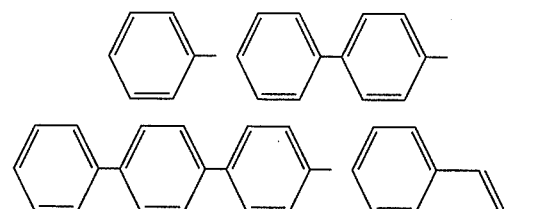
m, n are identical or different and are 0 or 1;
C, D are identical or different and are
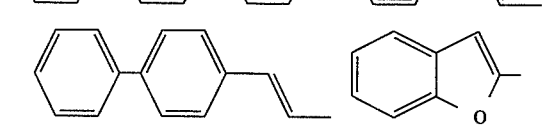
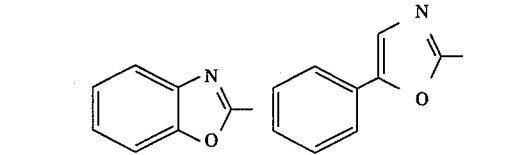
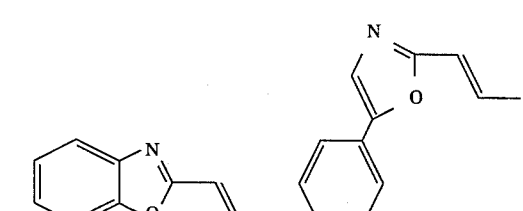
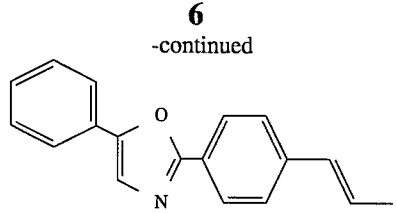
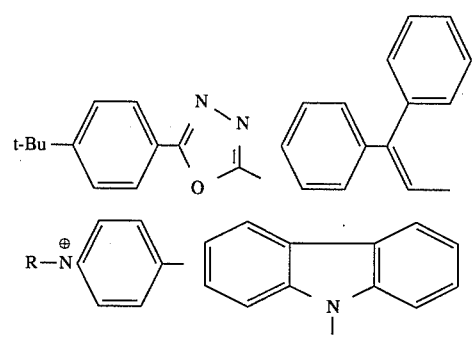
R=alkyl, C$_2$H$_4$SO$_3^-$
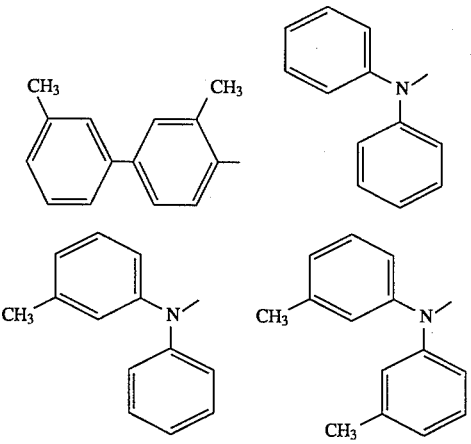
Very particular preference is given to polymers, in which the symbols and indices in the formula (I) have the following meanings:
A, B are identical or different and are
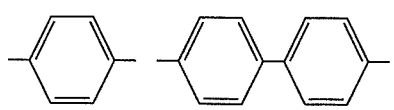
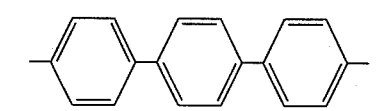
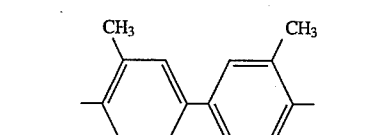
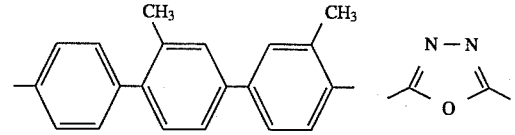

-continued

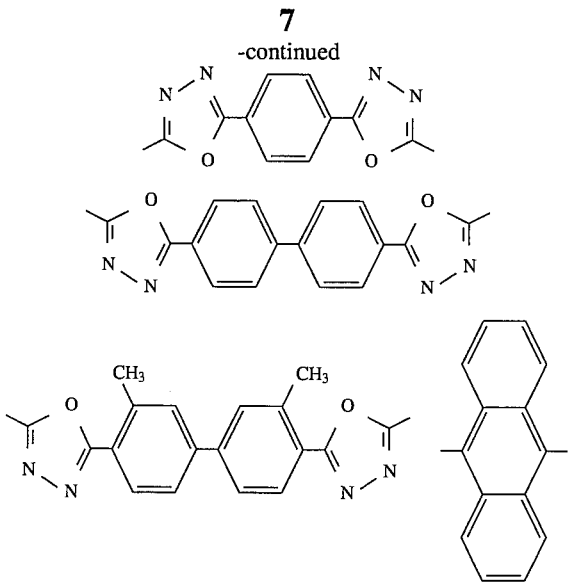

m+n is 0 or 1;
C, D are identical or different and are

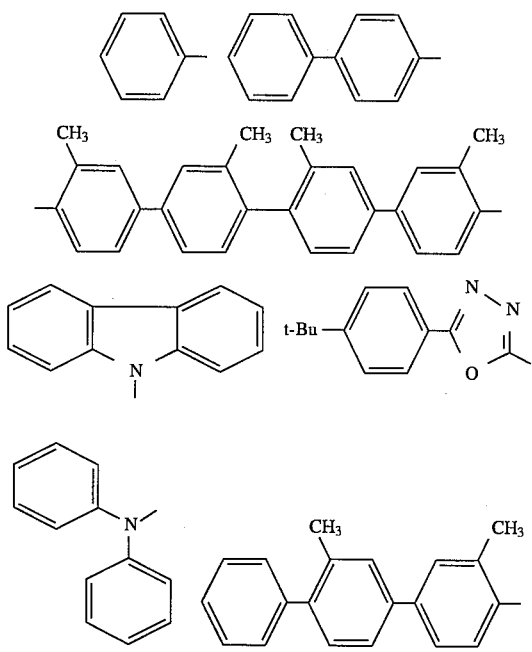

The polymers of the invention are homopolymers or copolymers, i.e. they can also have different recurring units of the formula (I).

The polymers of the invention also have a considerably increased solubility in organic solvents and good film-forming properties. This aids the production of electroluminescence devices and increases their life. In addition, the covalently bonded arrangement of the substituents via the spiro centers, perpendicular to the conjugated main chain, allows a molecular structure such that certain properties can be set without interfering with the conjugation in the main chain. Thus, the polymer chain can possess, for example, charge transport or charge injection properties, while the substituents possess light-emitting properties. The emission properties of the compounds used according to the invention can be adjusted over the entire range of the visible spectrum by selection of suitable substituents. The spatial proximity of the two halves which is fixed by the covalent linkage is here favorable for energy transmission (see, for example, B. Liphardt, W. Leüttke Liebigs Ann. Chem. 1981, 1118).

The polymers of the invention are well suited to achieving blue electroluminescence.

The preparation of the polymers of the invention can be carried out by literature methods known per se, as are described in the standard works on organic synthesis, e.g. Houben-Weyl, Methoden der Organischen Chemie, Georg-Thieme-Verlag, Stuttgart.

The preparation is here carried out under reaction conditions which are known and suitable for the specified reactions. Use can here also be made of variants known per se which are not mentioned further here.

Starting compounds used for preparing the polymers of the invention are generally monomers having a 9,9'-spiro-bifluorene center which are substituted in the 2,7 or, if desired, 2',7' positions.

Methods of synthesizing these monomers are based, for example, on the synthesis of 9,9'-spirobifluorene, for example from 2-bromobiphenyl and fluorenone via a Grignard synthesis as described by R. G. Clarkson, M. Gomberg, J. Am. Chem. Soc. 1930, 52, page 2881, which is subsequently further substituted in a suitable manner.

Functionalizations of 9,9'-spirobifluorene are described, for example, in J. H. Weisburger, E. K. Weisburger, F. E. Ray, J. Am. Chem. Soc. 1959, 72, 4253; F. K. Sutcliffe, H. M. Shahidi, D. Paterson, J. Soc. Dyers Colour 1978, 94, 306; and G. Haas, V. Prelog, Helv. Chim. Acta 1969, 52, 1202.

The desired substitution pattern of the 9,9'-spirobifluorene monomer is obtained considerably more favorably if the spiro linkage is carried out from suitably substituted starting materials, e.g. using 2,7-difunctionalized fluorenones and the 2',7' positions still free are then, if desired, further functionalized after formation of the spiro atom (e.g. by halogenation or acylation, with subsequent C—C linkage after conversion of the acetyl groups into aldehyde groups, or by heterocycle formation after conversion of the acetyl groups into carboxylic acid groups).

The further functionalization can be carried out by literature methods known per se as are described in standard works on organic synthesis, e.g. Houben-Weyl, Methoden der Organischen Chemie, Georg-Thieme Verlag, Stuttgart and in the appropriate volumes of the series "The Chemistry of Heterocyclic Compounds" by A. Weissberger and E. C. Taylor (editors).

For the synthesis of the groups A, B, C, D reference may be made, for example, to DE-A 23 44 732, 24 50 088, 24 29 093, 25 02 904, 26 36 684, 27 01 591 and 27 52 975 for compounds containing 1,4-phenylene groups, DE-A 26 41 724 for compounds containing pyrimidine-2,5-diyl groups; DE-A 40 26 223 and EP-A 03 91 203 for compounds containing pyridine-2,5-diyl groups; DE-A 32 31 462 for compounds containing pyridazine-3,6-diyl groups; N. Miyaura, T. Yanagi and A. Suzuki in Synthetic Communications 1981, 11, 513 to 519, DE-C-3 930 663, M. J. Sharp, W. Cheng, V. Snieckus in Tetrahedron Letters 1987, 28, 5093; G. W. Gray in J. Chem. Soc. Perkin Trans II 1989, 2041 and Mol. Cryst. Liq. Cryst. 1989, 172, 165, Mol. Cryst. Liq. Cryst. 1991, 204, 43 and 91; EP-A 0 449 015; WO 89/12039; WO 89/03821; EP-A 0 354 434 for the direct linkage of aromatics and heteroaromatics.

The preparation of disubstituted pyridines, disubstituted pyrazines, disubstituted pyrimidines and disubstituted pyridazines can be found, for example, in the appropriate volumes of the series "The Chemistry of Heterocyclic Compounds" by A. Weissberger and E. C. Taylor (editors).

Starting with the above monomers, the polymerization to give the polymers of the invention is possible by a number of methods.

For example, derivatives of 9,9'-spirobifluorene can be polymerized oxidatively (e.g. using FeCl$_3$, see, inter alia, P. Kovacic, N. B. Jones, Chem. Ber. 1987, 87, 357 to 379; M. Weda, T. Abe, H. Awano, Macromolecules 1992, 25, 5125) or electrochemically (see, for example, N. Saito, T. Kanbara, T. Sato, T. Yamamoto, Polym. Bull. 1993, 30, 285).

Likewise, the polymers of the invention can be prepared from 2,7-difunctionalized 9,9'-spirobifluorene derivatives. Dihaloaromatics can be polymerized using copper/triphenylphosphine (see, for example, G. W. Ebert, R. D. Rieke, J. Org. Chem. 1988, 53, 44829 or nickel/triphenylphosphine catalysis (see, for example, H. Matsumoto, S. Inaba, R. D. Rieke, J. Org. Chem. 1983, 48, 840).

Aromatic diboronic acids and aromatic dihalides or mixed aromatic halides/boronic acids can be polymerized by coupling reactions using palladium catalysis (see, for example, M. Miyaura, T. Yanagi, A. Suzuki, Synth. Commun. 1981, 11, 513; R. B. Miller, S. Dugar, Organometallics 1984, 3, 1261).

Aromatic distannanes can, for example as indicated in J. K. Stille, Angew. Chem. Int. Ed. Engl. 1986, 25, 508, be polymerized using palladium catalysis.

Furthermore, the abovementioned dibromo compounds can be converted into the dilithio or diGrignard compounds which are then polymerized with further dibromo compound by means of CuCl$_2$ (see, for example, G. Wittig, G. Klar, Liebigs Ann. Chem. 1967, 704, 91; H. A. Stabb, F. Bunny, Chem. Ber. 1967, 100, 293; T. Kaufmann, Angew. Chem. 1974, 86, 321 to 354) or by electron transfer of unsaturated 1,4-dihalo compounds (see, for example, S. K. Taylor, S. G. Bennett, K. J. Harz, L. K. Lashley, J. Org. Chem. 1981, 46, 2190).

However, the synthesis of the polymers of the invention can also be carried out by polymerization of a 2,7-difunctionalized 9,9'-spirobifluorene derivative with a further, suitably difunctionalized compound.

Thus, for example, 2,7-dibromo-9,9'-spirobifluorene can be polymerized with 4,4'-biphenylylbisboronic acid. In this way, it is possible to build up various heterocyclic units simultaneously with the polymerization step, for example the formation of oxadiazole units from difunctional carboxylic acid halides and difunctional carboxylic hydrazides or from the corresponding dicarboxylic acid and hydrazine sulfate (B. Schulz. E. Leibnitz, Acta Polymer 1992, 43, page 343; JP-A 05/178 990), or alternatively from dicarboxylic acid halides and bistetrazoles (C. A. Abshire, C. S. Marvel, Makromol. Chem. 1961, 44 to 46, page 388).

Copolymers can be prepared, for example, by jointly polymerizing different compounds of the formula (I).

The work-up is carried out by known methods with which those skilled in the art are familiar, as described, for example, in D. Braun, H. Cherdron, W. Kern, Praktikum der makromolekularen organischen Chemie, 3rd edition, H üthig Verlag, Heidelberg, 1979, p. 87 ff or R. J. Young, P. A. Lovell, Introduction to Polymers, Chapman & Hall, London 1991. For example, the reaction mixture can be filtered, diluted with aqueous acid, extracted and the crude product obtained after drying and taking off the solvent can be further purified by reprecipitation.

Terminal bromine atoms can, for example, be removed reductively using LiAlH$_4$ (see, for example, J. March, Advanced Organic Chemistry, 3rd edition, McGraw-Hill, p. 510).

The polymers of the invention can be used as electroluminescence materials.

The invention accordingly also provides for the use of polymers, comprising recurring units of the formula (I), as electroluminescence material.

For the purposes of the invention, electroluminescence materials are materials which can be used as active layer in an electroluminescence device. Active layer means that the layer is capable of emitting light on application of an electric field (light-emitting layer) and/or that it improves the injection and/or the transport of the positive and/or negative charges (charge injection or charge transport layer).

The invention accordingly also provides an electroluminescence material comprising one or more polymers which comprise recurring units of the formula (I).

The electroluminescence material usually contains one or more polymers, comprising recurring units of the formula (I) either as main component, i.e. to an extent of greater than 50% by weight, or as additive.

To be used as electroluminescence materials, the polymers of the invention are generally applied in the form of a film to a substrate by known methods with which those skilled in the art are familiar, such as casting, dipping or spin coating.

The invention accordingly further provides a process for producing an electroluminescence material, which comprises applying a polymer, comprising recurring units of the formula (I), in the form of a film to a substrate.

In addition, the invention provides an electroluminescence device having one or more active layers, wherein at least one of these active layers comprises one or more polymers of the invention. The active layer can, for example, be a lightemitting layer and/or a transport layer and/or a charge injection layer.

The general structure of such electroluminescence devices is described, for example, in U.S. Pat. Nos. 4,539,507 and 5,151,629. Electroluminescence devices containing polymers are described, for example, in WO 90/13148 or EP-A 0 443 861.

They usually contain an electroluminescing layer between a cathode and an anode, with at least one of the electrodes being transparent. In addition, an electron injection and/or electron transport layer can be introduced between the electroluminescing layer and the cathode, and/or a hole injection and hole transport layer can be introduced between the electroluminescing layer and the anode. The cathode can be, for example, Ca, Mg, Al, In, Mg/Ag. The anode can be, for example, Au or ITO (indium oxide/tin oxide) on a transparent substrate, for example of glass or a transparent polymer.

In operation, the cathode is placed at a negative potential compared with the anode. Electrons from the cathode are thus injected into the electron injection layer/electron transport layer or directly into the light-emitting layer. At the same time, holes from the anode are injected into the hole injection layer/hole transport layer or directly into the lightemitting layer.

The injected charge carriers move towards one another through the active layers under the action of the applied potential. This leads, at the interface between charge transport layer and light-emitting layer or within the lightemitting layer, to electron/hole pairs which recombine with emission of light.

The color of the emitted light can be varied by means of the compound used as light-emitting layer.

Electroluminescence devices are used, for example, as self-illuminating display elements such as control lamps, alphanumeric displays, signs, and in optoelectronic couplers.

The invention is illustrated by the examples, without it being restricted thereby.

EXAMPLES

A Monomer syntheses

Example 1

Synthesis of 2,7-dibromo-9,9'-spirobifluorene

A Grignard reagent prepared from 0.72 g (30 mmol) of magnesium turnings and 5.1 ml (30 mmol) of 2-bromobiphenyl in 15 ml of diethyl ether is added dropwise over the course of 2 hours while stirring (in an ultrasonic bath) to a boiling suspension of 10.0 g (29.6 mmol) of 2,7-dibromo-9-fluorenone in 1 00 ml of dry diethyl ether. After addition is complete, the mixture is boiled for a further 3 hours. After cooling overnight, the precipitate formed is filtered off with suction and washed with cold ether. The magnesium complex filtered off is hydrolyzed in a solution of 15 g of ammonium chloride in 250 ml of ice water. After 1 hour, the 9-(2-biphenylyl)-2,7-dibromo-9-fluorenol formed is filtered off with suction, washed with water and sucked dry. For the ring closure reaction, the dried fluorenol is boiled in 100 ml of glacial acetic acid, after addition of 3 drops of concentrated hydrochloric acid, for 6 hours. The mixture is allowed to crystallize overnight, the product formed is filtered off with suction and washed with glacial acetic acid and water.

Yield: 11 g (77%) of 2,7-dibromo-9,9'-spirobifluorene. It can be further purified by recrystallization from THF.

$^1$H-NMR (CDCl$_3$, ppm): 6.73 (d, J=7.63 Hz, 2H, H-1',8'); 6.84 (d, J=1.83 Hz, 2H, H-1,8); 7.15 (td, J=7.63, 1.22 Hz, 2H, H-2',7'); 7.41 (td, J=7.63, 1.22 Hz, 2H, H-3',6'); 7.48 (dd, J=8.24, 1.83 Hz, 2H, H-3,6); 7.67 (d, J=8.24; 2H; H-4,5); 7.85 (d, J=7.63, 2H, H-4',5').

Example 2

Synthesis of 2,7-dicarbethoxy-9,9'-spirobifluorene

A Grignard reagent prepared from 0.97 g (40 mmol) of magnesium turnings and 9.32 g (6.8 ml, 40 mmol) of 2-bromobiphenyl in 50 ml of dry diethyl ether is added dropwise over the course of 2 hours to a boiling solution of 13 g (40 mmol) of 2,7-dicarbethoxy-9-fluorenone in 100 ml of dry diethyl ether. After addition is complete, the mixture is boiled for a further 3 hours. After cooling overnight, the precipitate formed is filtered off with suction and washed with cold ether. The magnesium complex filtered off is hydrolyzed in a solution of 15 g of ammonium chloride in 250 ml of ice water. After 1 hour, the 9-(2-biphenylyl)-2,7-dicarbethoxy-9-fluorenol formed is filtered off with suction, washed with water and sucked dry. For the ring closure reaction, the dried fluorenol is boiled in 100 ml of glacial acetic acid, after addition of 3 drops of concentrated hydrochloric acid, for 6 hours. The mixture is allowed to crystallize overnight, the product formed is filtered off with suction and washed with glacial acetic acid and water.

Yield: 15.1 g (82%) of 2,7-dicarbethoxy-9,9'-spirobifluorene. It can be further purified by recrystallization from ethanol.

$^1$H-NMR (CDCl$_3$, ppm): 1.30 (t, J=7.12 Hz, 6H, ester-CH$_3$); 4.27 (q, J=7.12 Hz, 4H, ester-CH$_2$); 6.68 (d, J=7.63 Hz, 2H, H-1',8'); 7.11 (td, J=7.48, 1.22 Hz, 2H, H-2',7'); 7.40 (td, J=7.48, 1.22 Hz, 4H, H-1, 8,3',6'); 7.89 (dt, J=7.63, 0.92 Hz, 2H, H-4',5'); 7.94 (dd, J=7.93, 0.6 Hz, 2H, H-4,5); 8.12 (dd, J=7.93, 1.53 Hz, 2H, H-3,6).

B Polymerizations

Example 3

Polymerization of 2,7-dibromo-9,9'-spirobifluorene by the method of Yamamoto using Ni(0) to give poly-2,7-(9,9'-spirobifluoren)ylene (Polymer 1)

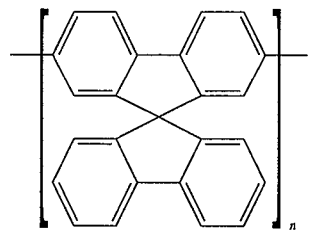

Under argon, a solution of 1.517 g of 2,7-dibromo-9,9'-spirobifluorene in 30 ml of dry THF is prepared and heated to 60° C. The warm solution is quickly added under protective gas to a refluxing mixture, likewise under protective gas, of 825 mg of Ni(cod)$_2$, 470 mg of 2,2'-bipyridyl and 0.4 ml of 1,5-cyclooctadiene (COD) in 20 ml of dry THF. The polymerization starts immediately, with the deep blue reaction mixture becoming red. The mixture is allowed to boil at reflux for a further 6 hours and is subsequently cooled to room temperature. The red polymer is filtered off with suction and washed with THF, dilute hydrochloric acid and water.

Extraction with 200 ml of chloroform gives a first soluble polymer fraction (further soluble fractions are obtainable by extraction, for example, with 1,2-dichloroethane and 1-chloronaphthalene) which is purified by shaking with ethylenediaminetetraacetic acid (3× with an aqueous solution adjusted to pH 7–8 with ammonia, once at pH 3) and subsequent shaking with dilute hydrochloric acid and water. The dried chloroform solution is evaporated to 10 ml and the polymer is precipitated by dropwise addition to 70 ml of methanol. The polymer obtained is yellowish.

$^1$H-NMR (CDCl$_3$, ppm): 6.63–6.68 (2H, H-1,8); 6.71–6.75 (2H, H-1',8'); 700–7.10 (2H, H-2',7'); 7.21–7.38 (4H, H-3,3',6,6'); 7.59–7.70 (2H, H-4',5'); 7.75–7.82 (2H, H-4,5).

Example 4

Polymerization of 2,7-dibromo-9,9'-spirobifluorene with 4,4'-biphenyldiboronic acid to give poly[2,7-(9,9'-spirobifluorenylene)-4,4'-biphenylene] (Polymer 2)

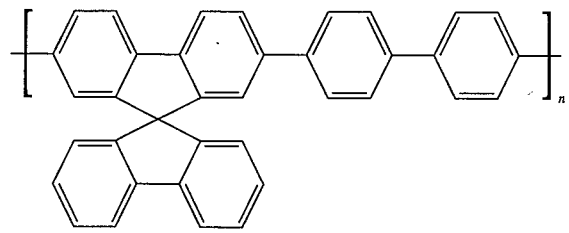

948 mg (2 mmol) of 2,7-dibromo-9,9'-spirobifluorene and 483 mg (2 mmol) of 4,4'-biphenyldiboronic acid are added to a mixture of 25 ml of THF and 10 ml of ethanol. 20 ml of 1 molar aqueous potassium carbonate solution are added thereto. The mixture is refluxed under nitrogen and 50 mg of tetrakis(triphenylphosphine)palladium(0) dissolved in 5 ml of THF are added. After refluxing for 24 hours, the mixture is cooled to room temperature. The pale yellow polymer formed is filtered off with suction, boiled with dilute hydrochloric acid for 2 hours and after being again filtered off with suction is washed free of acid with water. Extraction with 100 ml of chloroform gives a first soluble polymer fraction (further soluble fractions are obtainable by extraction, for example, with 1,2-dichloroethane and 1-chloronaphthalene).

$^1$H-NMR (CDCl$_3$, ppm): 6.75–6.85 (2H); 6.94 (2H, H-1, 8); 7.05–7.15 (2H); 7.32–7.39 (2H); 7.42–7.52 (8H); 7.61–7.68 (2H); 7.81–7.87 (2H); 7.88–7.92 (2H).

Example 5

Photoluminescence measurement on poly-2,7-(9,9'-spirobifluoren)ylene (Polymer 1)

A solution of poly-2,7-(9,9'-spirobifluoren)ylene in chloroform (5 mg/ml) is applied by spin coating at 1000 rpm to a quartz support. On excitation with light having a wavelength <400 nm, the polymer film shows a homogeneous blue fluorescence. The fluorescence spectrum (Hitachi F4500 spectrofluorimeter, excitation at 360 nm) of the polymer film thus prepared is shown in FIG. 1. A comparison with the fluorescence spectrum of the polymer 1 in dilute solution (<10$^{-4}$ mol/l in chloroform) gives a bathochromic shift of 10 nm for the film with maintenance of the spectral characteristics of the dilute solution (see FIG. 1).

Example 6

Photoluminescence measurement on poly[2,7-(9,9'-spirobifluorenylene)-4,4'-biphenylene] (Polymer 2)

A solution of poly[2,7-(9,9'-spirobifluorenylene)-4,4'-biphenylene] in chloroform (5 mg/ml) is applied by spin coating at 1000 rpm to a quartz support. On excitation with light having a wavelength<400 nm, the polymer film shows a homogeneous blue fluorescence. The fluorescence spectrum (Hitachi F4500 spectrofluorimeter, excitation at 360 nm) of the solid polymer film thus prepared is shown in FIG. 2. A comparison with the fluorescence spectrum of the polymer 2 in dilute solution (<10$^{-4}$ mol/l in chloroform) gives a bathochromic shift of 15 nm for the film with maintenance of the spectral characteristics of the dilute solution (see FIG. 2).

Electroluminescence device

A solution of the polymer to be measured in chloroform (concentration: 15 mg/ml) is, under nitrogen, applied by spin coating at 1,000 rpm to a glass support coated with ITO (indium-tin oxide) (structured, strips 2 mm wide). The glass support is transferred, with maintenance of the protective gas atmosphere, via a lock into a high vacuum vapor deposition unit. At 2×10$^{-5}$ mbar, Ca strips (2 mm wide, 230 nm thick) are vapor deposited using a mask onto the polymer layer at right angles to the ITO strips. The device thus obtained, ITO/polymer/Ca, is placed in a sample holder and the electrodes are connected to a power source via spring finger connectors, with an ITO strip being given positive polarity and a Ca strip being given negative polarity. On application of a sufficiently high potential, electroluminescence is observed at the corresponding matrix element.

We claim:

1. A conjugated polymer comprising 2 to 1000 recurring units of the formula (I),

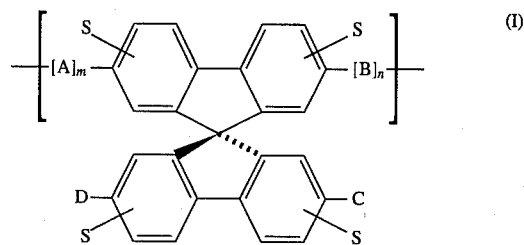

where the symbols and indices have the following meanings:

A, B, C, D are identical or different and are each from one to fifteen identical or different arylene and/or heteroarylene and/or vinylene groups which, like the spirobifluorene skeleton itself, may be unsubstituted or substituted;

S are identical or different and are each H or a substituent;

m, n are 0 or 1.

2. A polymer as claimed in claim 1, wherein the symbols and indices in the formula (I) have the following meanings:

S are identical or different and are R$^1$, R$^2$, R$^3$ and/or R$^4$;

A,B are identical or different and are

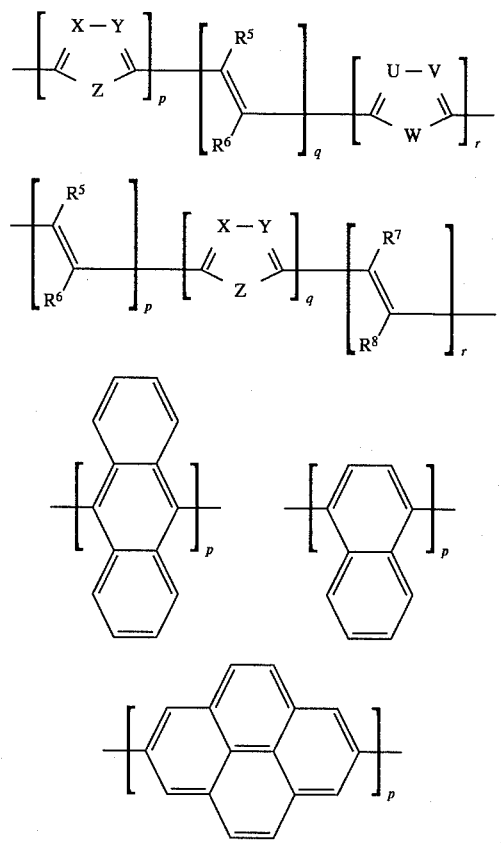

15
-continued

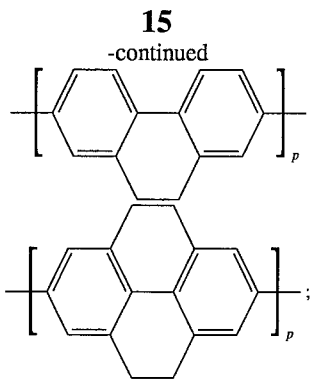

X, Y, U, V are identical or different and are $CR^5$, N;

Z, W are identical or different and are —O—, —S—, —$NR^5$—, —$CR^5R^6$—, —$CR^5$=$CR^6$—, —$CR^5$=N—;

p, q, r are identical or different and are 0, 1 to 5;

$R^1$, $R^2$, $R^3$, $R^4$, $R^5$, $R^6$, $R^7$, $R^8$ are identical or different and are each H, a straight-chain or branched alkyl, alkoxy or ester group having from 1 to 22 carbon atoms, aryl and/or aryloxy groups, where the aromatic can be substituted by $C_1$-$C_{22}$-alkyl, $C_1$-$C_{22}$-alkoxy, Br, Cl, F, CN, and/or $NO_2$, Br, Cl, F, CN, $NO_2$, $CF_3$;

C, D are identical or different and are

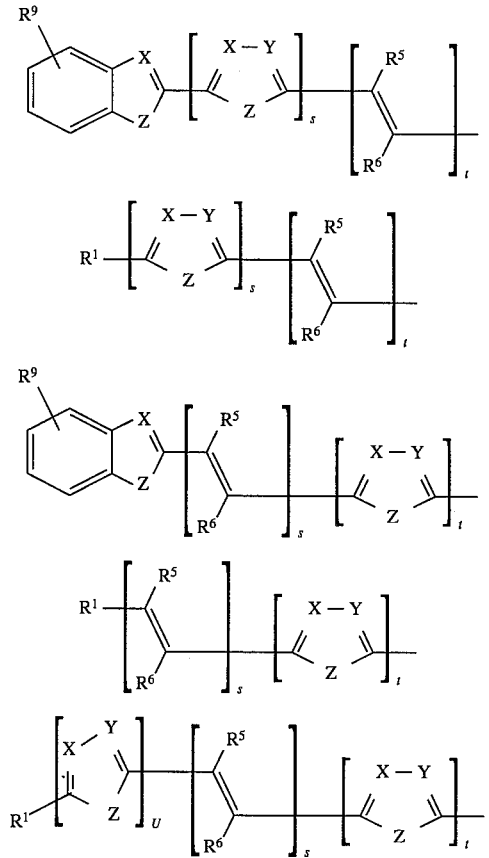

16
-continued

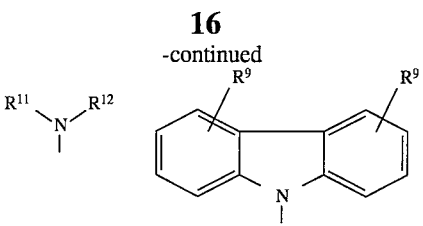

$R^9$ are identical or different and are each H, an unbranched or branched alkyl or alkoxy group having from 1 to 22 carbon atoms, —CN, —$NO_2$, —$NR^{11}R^{12}$, phenyl, biphenyl, 1-naphthyl, 2-naphthyl, 2-thienyl, 2-furanyl, where aryls and heteroaryls can bear a further substituent $R^9$;

X, Y are identical or different and are =$CR^5$—, =N—;

Z are identical or different and are —O—, —S—, —$NR^{11}$—, $CR^5R^6$, —$CR^5$=$CR^6$—, —$CR^5$=N—;

$R^{11}$, $R^{12}$ are identical or different and are each H, an unbranched or branched alkyl group having from 1 to 22 carbon atoms, phenyl, 3-methylphenyl, biphenyl, 1-naphthyl, 2-naphthyl.

3. A polymer as claimed in claim 1, wherein the symbols and indices in the formula (I) have the following meanings:

A, B are identical or different and are

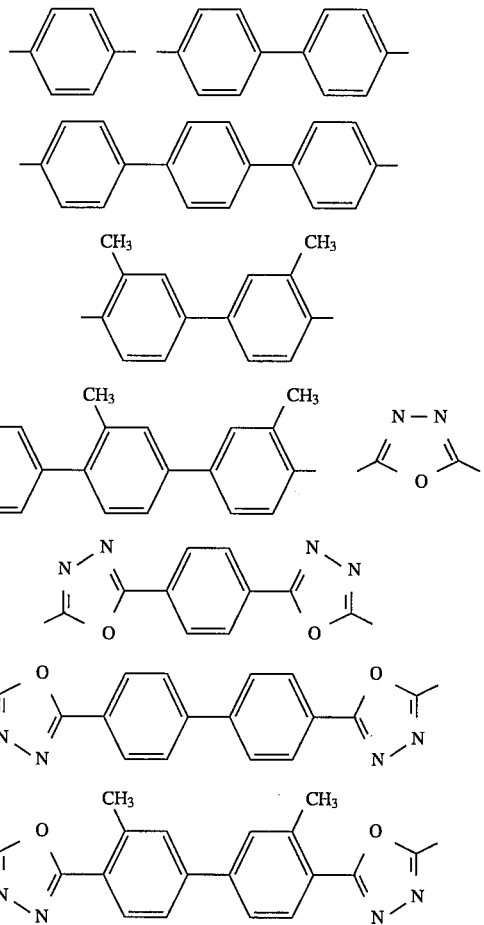

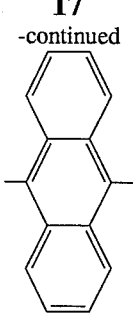
m, n are identical or different and are 0 or 1;
C, D are identical or different and are
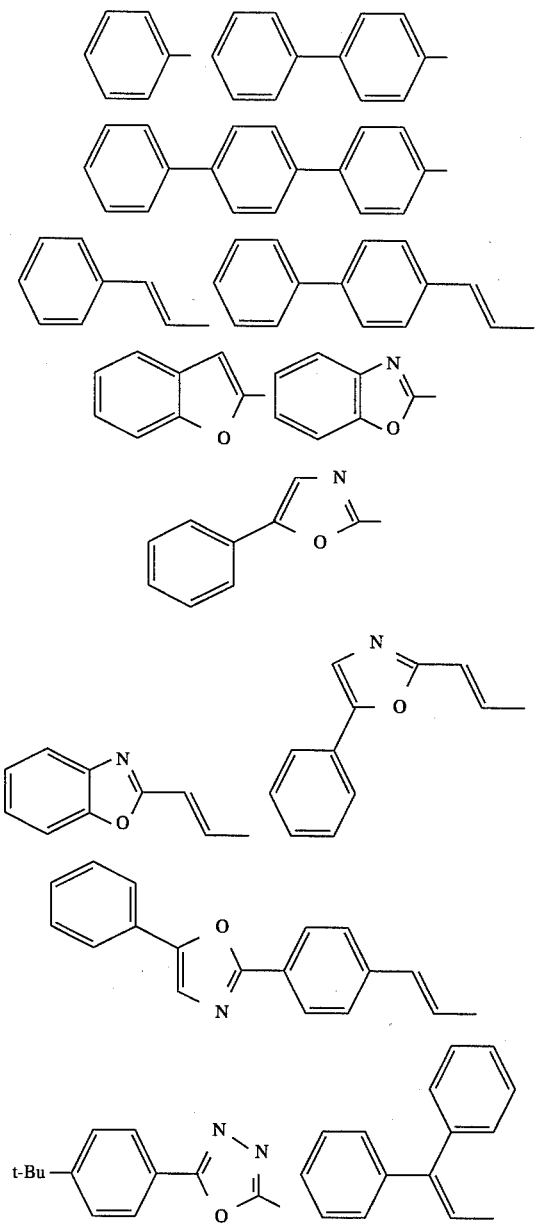
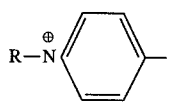
R=alkyl, $C_2H_4SO_3^-$
4. A polymer as claimed in claim 1, wherein the symbols and indices in the formula (I) have the following meanings:
A, B are identical or different and are
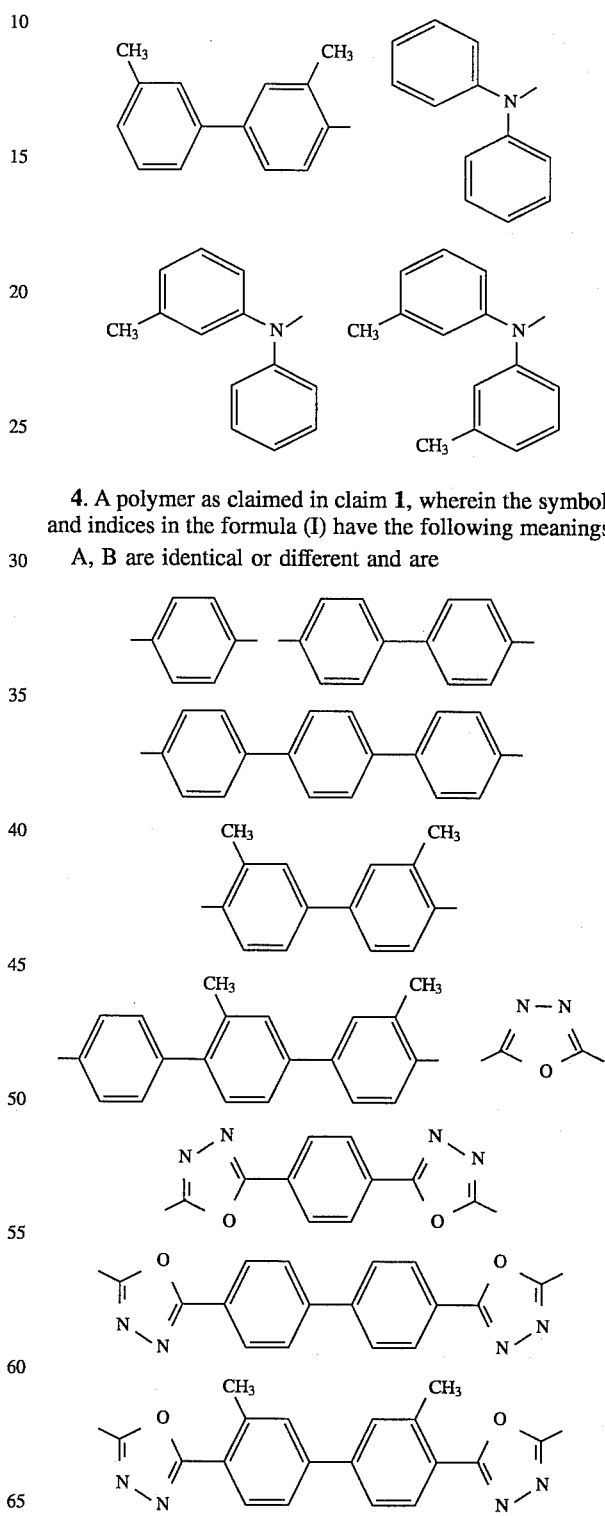

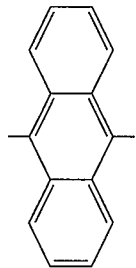

m+n is 0 or 1;

C, D are identical or different and are

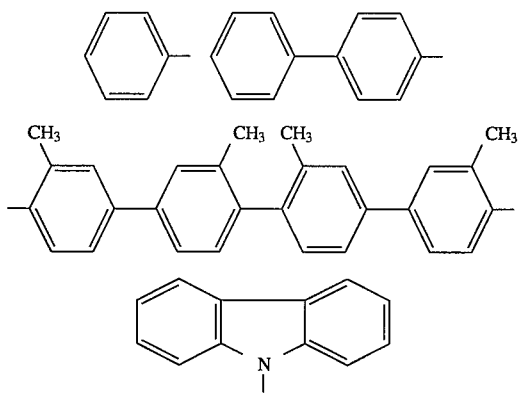

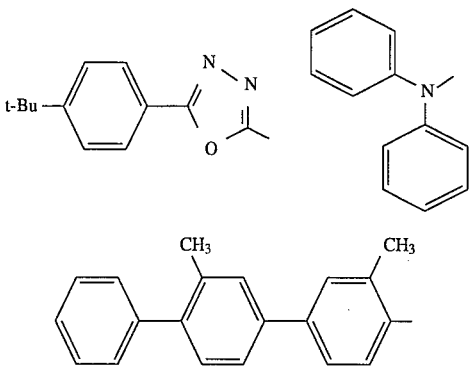

5. A polymer as claimed in claim 1, which is a copolymer.

6. An electroluminescence material comprising a polymer as claimed in claim 1.

7. A process for producing an electroluminescence material, which comprises applying a polymer as claimed in claim 1 in the form of a film to a substrate.

8. An electroluminescence device comprising one or more active layers, wherein at least one of these active layers comprises a polymer as claimed in claim 1 as electroluminescence material.

* * * * *